US008542877B2

(12) United States Patent
Jeanne et al.

(10) Patent No.: US 8,542,877 B2
(45) Date of Patent: Sep. 24, 2013

(54) PROCESSING IMAGES OF AT LEAST ONE LIVING BEING

(75) Inventors: Vincent Jeanne, Eindhoven (NL); Frederik Jan De Bruijn, Eindhoven (NL); Ruud Vlutters, Eindhoven (NL); Giovanni Cennini, Eindhoven (NL); Dmitri Chestakov, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 99 days.

(21) Appl. No.: 13/254,200

(22) PCT Filed: Mar. 1, 2010

(86) PCT No.: PCT/IB2010/050870
§ 371 (c)(1),
(2), (4) Date: Sep. 1, 2011

(87) PCT Pub. No.: WO2010/100594
PCT Pub. Date: Sep. 10, 2010

(65) Prior Publication Data
US 2011/0311119 A1  Dec. 22, 2011

(30) Foreign Application Priority Data
Mar. 6, 2009 (EP) ................................. 09154493

(51) Int. Cl.
*G06K 9/00* (2006.01)
(52) U.S. Cl.
USPC .......................................... 382/103; 382/128
(58) Field of Classification Search
None
See application file for complete search history.

(56) References Cited

U.S. PATENT DOCUMENTS 5,719,950 A * 2/1998 Osten et al. .................... 382/115
2011/0251493 A1 * 10/2011 Poh et al. ....................... 600/477

FOREIGN PATENT DOCUMENTS

| CN | 101112307 A | 1/2008 |
| WO | 8804152 A1 | 6/1988 |
| WO | 0167960 A2 | 9/2001 |

OTHER PUBLICATIONS

Verkruysse et al: "Remote Plethysmographic Imaging Using Ambient Light"; Optics Express, OSA, vol. 16, No. 26, Dec. 22, 2008, pp. 21434-21445.
Hulsbusch, M.: "Ein Bildgestutztes, Funktionelles Verfahren Zur Optoelektronischen Erfassung Der Hautperfusion"; Dissertation Technischen Hochschule Aachen, Jan. 28, 2008, 145 page Document.
Wieringa et al: "Contactless Multiple Wavelength Photoplethysmographic Imaging: A First Step Toward "SpO2 Camera" Technology"; Annals of Biomedical Engineering, vol. 33, No. 8, Aug. 1, 2005, pp. 1034-1041.

(Continued)

Primary Examiner — Samir Ahmed
Assistant Examiner — Siamak Harandi

(57) ABSTRACT

A method of processing images of at least one living being, includes obtaining a sequence (19) of digital images taken at consecutive points in time. At least one measurement zone (26) comprising a plurality of image points is selected. For each measurement zone (26), a signal (28,30) representative of at least variations in a time-varying value of a combination of pixel values at least a number of the image points for use in determining at least one of a presence and a frequency value of at least one peak in a spectrum of the signal (28,30) corresponding to a frequency of a periodic physiological phenomenon is obtained. The step (25) of selecting at least one measurement zone (26) includes analyzing information based on pixel data of a plurality of image parts in at least one of the images (19), each image part including at least one image point, and selecting each measurement zone (26) from contiguous parts determined to have similar characteristics.

28 Claims, 3 Drawing Sheets

(56) References Cited

OTHER PUBLICATIONS

Viola et al: "Robust Real-Time Object Detection"; Second International Workshop on Statistical and Computational Theories of Vision-Modeling, Learning, Computing, and Sampling; Vancouver, CA, Jul. 13, 2001, 25 page Document.

Lucchese et al: "Color Image Segmentation: A State-Of-The-Art Survey"; Proceedings of the Indian National Science Academy, New Dehli, India, Part A. Physical Sciences, vol. 67, No. 2, Mar. 1, 2001, pp. 207-221.

De Hann et al: "True-Motion Estimation With 3-D Recursive Search Block Matching"; IEEE Transactions on Circuits and Systems for Video Technology, vol. 3, No. 5, Oct. 1993, pp. 368-379.

Takano et al: "Heart Rate Measurement Based on a Time-Lapse Image"; Medical Engineering & Physics 29, 2007, pp. 853-857.

Yang et al: "Vital Sign Estimation From Passive Thermal Video"; IEEE Conference on Computer Vision and Pattern Recognition, Jun. 2008, 8 page Document.

* cited by examiner

PROCESSING IMAGES OF AT LEAST ONE LIVING BEING

FIELD OF THE INVENTION

The invention relates to a method of processing images of at least one living being, including:
  obtaining a sequence of digital images taken at consecutive points in time;
  selecting at least one measurement zone comprising a plurality of image points; and
  for each measurement zone, obtaining a signal representative of at least variations in a time-varying value of a combination of pixel values at least a number of the image points for use in determining at least one of a presence and a frequency value of at least one peak in a spectrum of the signal corresponding to a frequency of a periodic physiological phenomenon.

The invention also relates to a system for processing images of at least one living being, including:
  an interface for obtaining data representative of a sequence of digital images taken at consecutive points in time; and
  an image data processing system, configured to:
  select at least one measurement zone comprising a plurality of image points; and
  for each measurement zone, to obtain a signal representative of at least variations in a time-varying value of a combination of pixel values at least a number of the image points for use in determining at least one of a presence and a frequency value of at least one peak in a spectrum of the signal corresponding to a frequency of a periodic physiological phenomenon.

The invention also relates to a computer program.

BACKGROUND OF THE INVENTION

Verkruysse et al., "Remote plethysmographic imaging using ambient light", *Optics Express*, 16 (26), 22 Dec. 2008, pp. 21434-21445 demonstrates that photo-plethysmography signals can be measure remotely on the human face with normal ambient light as the source and a simple digital, consumer-level photo camera in movie mode. After setting the camera in movie mode, volunteers were asked to sit, stand or lie down to minimize any movements. Color movies were saved by the camera and transferred to a personal computer. Pixel values for the red, green and blue channels were read for each movie frame, providing a set of PV(x,y,t), where x and y are horizontal and vertical positions, respectively and t is time corresponding to the frame rate. Using a graphic user interface, regions of interest (ROI) were selected in a still (selected from the movie) and the raw signal $PV_{raw}(t)$ was calculated as the average of all pixel values in the ROI. Fast Fourier Transforms were performed to determine the power and phase spectra. It is stated that selection of the ROI is not critical for the heart rate determination. It is also stated that limits to the spatial resolution of photoplethysmography images due to movement artifacts may be solvable by improved positioning of the volunteers, software to laterally synchronize the frames and more homogeneous illumination to reduce shading artifacts.

A problem of the known method is that it uses a supervisor to select the ROI of the part of the image he knows corresponds to the living person.

It is an object of the invention to provide a method, system and computer program of the types mentioned above in the opening paragraphs that require little or no human supervision in order to provide good results.

This object is achieved by the method according to the invention, which includes:
  obtaining a sequence of digital images taken at consecutive points in time;
  selecting at least one measurement zone comprising a plurality of image points; and
  for each measurement zone, obtaining a signal representative of at least variations in a time-varying value of a combination of pixel values at least a number of the image points for use in determining at least one of a presence and a frequency value of at least one peak in a spectrum of the signal corresponding to a frequency of a periodic physiological phenomenon. The step of selecting at least one measurement zone includes analyzing information based on pixel data of a plurality of image parts in at least one of the images, each image part including at least one image point, and selecting each measurement zone from contiguous parts determined to have similar characteristics.

Analyzing information based on pixel data of a plurality of image parts in at least one of the images, where each image part includes at least one image point, can be conducted automatically, as can clustering those parts determined to have similar characteristics. Thus, this method is suitable for unsupervised execution. Selecting contiguous parts determined to have similar characteristics results in the determination of a region of the image with homogeneous characteristics. If these characteristics are similar according to an analysis in the spatial domain, a better selection of a homogeneous zone which will form the measurement zone can be made. Even if the body part corresponding to the measurement zone does not remain exactly in position throughout the sequence of images, the pixel intensities in the measurement zone will not vary appreciably due to such variations in position. This improves the quality of the spectrum of signal corresponding to the time-varying value of the combination of pixel values at least a number of the image points, so that reliable identifications of signal peaks corresponding to heart beat or breathing rate can be made. The effect is not dependent on particular lighting conditions, making the method more robust and more suitable for remote sensing applications. By using data representative of at least part of a spectrum of a time-varying value of a combination of pixel values at least a number of the image points, a large amount of noise can be eliminated. This allows one to use images that are obtained by capturing light reflected off a living subject. Such images can be obtained with a relatively cheap camera or sensor array. By contrast, if one were to determine the spectrum of each pixel individually and then cluster the values of the peaks, one would have to use images obtained using a very sensitive imaging device, e.g. a passive thermal imaging device.

An embodiment of the method includes performing image segmentation on at least one of the sequence of digital images to select pixel data for the analysis included in the selection step.

An effect is that the amount of pixel data that has to be analyzed in the selection step is reduced, since only certain promising ones of the segments obtained in the segmentation step need be processed.

In a variant of this embodiment, the image segmentation is performed using an algorithm for recognizing image parts corresponding to at least one type of body part of a living being.

This variant selects those image parts corresponding to parts of living beings that are suitable for an analysis to determine at least one of a presence and a frequency value of at least one peak in a spectrum of the average brightness signal corresponding to the frequency of a periodic physiological phenomenon. In principle, the method is based on the fact that the intensity of light reflected off skin varies with the frequency of periodic physiological phenomenon, i.e. the heart rate and respiration rate. Thus, a segmentation algorithm aimed at detecting skin, or body parts with shapes corresponding to those of body parts that are generally uncovered (e.g. the face of a human being) provides a pre-selection of suitable image segments, within which one or more homogeneous measurement zones are selected.

An embodiment of the method includes using a tracking algorithm to place at least one of the measurement zone and an image segment including the measurement zone in each of a plurality of the images in the sequence.

This embodiment takes account of the fact that even a homogeneous measurement zone may be affected by larger movements. The tracking algorithm allows the measurement zone to move with the actual body part it represents. Thus, signal artifacts arising from inhomogeneous image parts moving into the measurement zone are largely avoided. This improves the signal to noise ratio of the signal components corresponding to the periodic physiological phenomena.

In an embodiment, the sequence of digital images is caused to be captured by a camera upon completion of an initialization phase, the initialization phase including:
  measuring periodic intensity fluctuations in at least parts of images acquired by the camera whilst camera settings are varied, and
  selecting values of the camera settings at which measured periodic intensity fluctuations in at least a range of frequencies are determined to be minimal.

This embodiment allows one to remove sources of periodic disturbances, e.g. at the mains frequency. Typically, such disturbances correspond to periodic fluctuations in ambient lighting. Because the method is suitable for remote imaging, these disturbances play more of a role than would be the case if one were to use e.g. an infrared light source and camera. Intensity fluctuation measurements can be limited to one color component or be based on a weighted sum of some or all of the color components comprised in the pixel data. Suitable camera settings to be varied include the frame rate, exposure time, camera gain and pixel clock.

An embodiment of the method includes determining a correction signal corresponding to a time-varying value of a combination of pixel values at least a number of image points in an image part other than the measurement zone, and
  decorrelating at least one of the pixel data of the images in at least the measurement zone and the time-varying value of the combination of pixel values at least a number of the image points in the measurement zone from the correction signal.

This embodiment allows one to move non-periodic disturbances from the analysis, further improving the signal to noise ratio of the signal components due to periodic physiological phenomena. An example would be the reflections of a television signal in the face of a person watching television whilst the sequence of images is captured. It is noted that the image part other than the measurement zone may be a larger image part that also encompasses the measurement zone.

In an embodiment of the method, an output representative of whether the presence of at least one peak in the spectrum corresponding to a frequency of the periodic physiological phenomenon is detected is used to control a device arranged to perform a function conditional on detecting a presence of at least one living being of at least one kind.

An effect is that it is possible to verify that a living person is actually present in an unobtrusive way.

In a variant, the output is provided to a conditional access system for use in an authentication operation.

An effect is that it is no longer possible to fool the conditional access system that a particular person is present. For example, it is not possible to provide a fingerprint detector with a wax cast of an absent person's finger, or to fool a face recognition system with a photograph of an absent person. Thus, this method is particularly suitable for use in conjunction with a biometric conditional access system.

In an embodiment of the method, the frequency value of at least one peak in the spectrum corresponding to the frequency of the periodic physiological phenomenon is determined and a system for providing perceptible output is caused to adapt its output in dependence on the frequency signal.

Thus, this embodiment is particular suited to providing bio-feedback, e.g. in an ambient system or in a gaming or fitness environment.

An embodiment of the method includes providing a gating signal based on the signal corresponding to at least the variation in the time-varying value of the combination of pixel values at least a number of the image points to an imaging system.

This embodiment is suitable for use with imaging systems such as MRI or CT systems, wherein a person is placed in a scanner. In such imaging systems, a gating signal is often required in order to obtain a still image of e.g. a heart. An unobtrusive heart or respiration rate determination is preferred to lower the stress level of the person being imaged. Furthermore, there are no wires or probes that might affect the imaging system.

An embodiment of the method includes:
  selecting a plurality of measurement zones;
  for each measurement zone, obtaining a signal representative of at least variations in a time-varying value of the combination of pixel values at least a number of the image points and determining the frequency value of at least one peak in a spectrum of the signal corresponding to a frequency of a periodic physiological phenomenon; and
  detecting how many living beings are represented in the sequence of images by comparing the frequency values.

This method is suitable for an image segmentation method for example. It allows one to discern between different people in the images. Other applications include image analysis systems for crowd control, for example.

According to another aspect, the system for processing images of at least one living being according to the invention includes:
  an interface for obtaining data representative of a sequence of digital images taken at consecutive points in time; and
  an image data processing system, configured to:
  select at least one measurement zone comprising a plurality of image points; and
  for each measurement zone, to obtain a signal representative of at least variations in a time-varying value of the combination of pixel values at least a number of the image points for use in determining at least one of a presence and a frequency value of at least one peak in a spectrum of the signal corresponding to a frequency of a periodic physiological phenomenon, wherein the image data processing system is configured to select the at least one measurement zone by analyzing information based on pixel data of a plurality of image parts in at least one of the images, each image part including at least one image point, and to select each measurement zone from contiguous parts determined to have similar characteristics.

In an embodiment, the system is configured to carry out a method according to the invention.

According to another aspect of the invention, there is provided a computer programme including a set of instructions capable, when incorporated in a machine-readable medium, of causing a system having information processing capabilities to perform a method according to the invention.

BRIEF DESCRIPTION OF THE DRAWINGS

The invention will be explained in further detail with reference to the accompanying drawings, in which.

DETAILED DESCRIPTION

Figure 1:
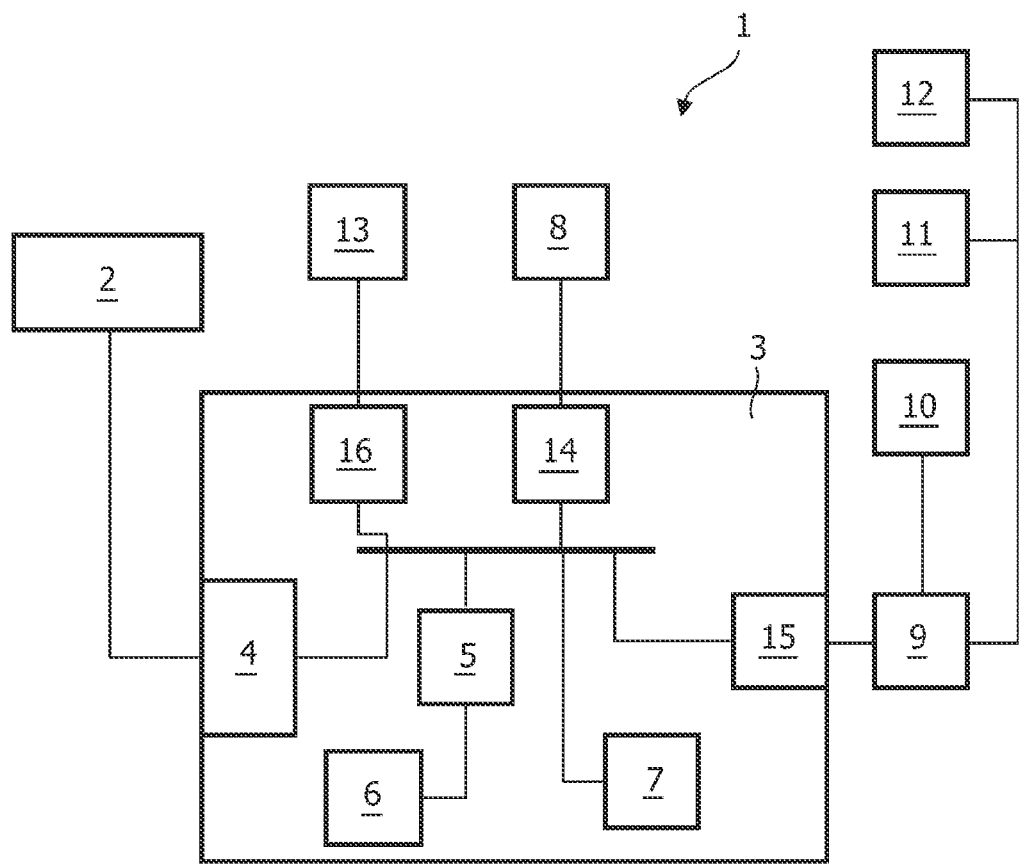
FIG. 1 is a schematic diagram of a system arranged to adapt its output in dependence on whether it has detected the presence of a living being or on the heart rate or respiration rate of a living being.

Referring to FIG. 1, an example is given here of a first system 1 that is arranged to process a sequence of images. The first system 1 carries out this processing in order to determine at least one of the presence and a frequency value of at least one peak in a spectrum of a signal based on the pixel data of the images corresponding to a frequency of a periodic physiological phenomenon. The presence of a living being is inferred from the presence of the peak, and used as a binary input for one or more system processes. The frequency of the peak is used as an input in at least one of those processes.

The first system 1 includes a digital camera 2 arranged to record a sequence of digital images in quick succession. The first system 1 further includes a data processing device 3 which is in communication with the digital camera 2 for the purpose of obtaining the image data, but also to control the operation of the digital camera 2, as will be explained.

The digital image data captured by the digital camera 2 is passed to the data processing device 3 via an interface 4 of the data processing device 3. In the illustrated embodiment, the data processing device 3 includes a processing unit 5 and main memory 6, as well as a data storage device 7 for non-volatile storage of data, e.g. the digital image data and software enabling the data processing device 3 to process the image data and control a number of peripheral devices.

In the illustrated embodiment, the peripheral devices include a television set 8; an ambient system including a controller 9 and lighting units 10-12; and a biometric scanning device 13. All are connected to the data processing device 3 via respective interfaces 14-16. These peripheral devices are just examples of peripheral devices that can be controlled in dependence on the results of one or more variants of an image processing method to be described with reference to FIG. 2.

This method is used to determine the presence of a living being, i.e. a human or animal, in a scene captured by the digital camera 2, by generating a signal on the basis of image data corresponding to a patch of skin, which signal varies with the frequency of a periodic physiological phenomenon, e.g. the heartbeat or breathing of a human being.

The human skin can be modeled as a two-layered object, one layer being the epidermis (a thin surface layer) and the other the dermis (a thicker layer underneath the epidermis). Approximately 5% of an incoming ray of light is reflected in the epidermis, which is the case for all wavelengths and skin colors. The remaining light is scattered and absorbed within the two skin layers in a phenomenon known as body reflectance (described in the Dichromatic Reflection Model). The epidermis behaves like an optical filter, mainly absorbing light. In the dermis, light is both scattered and absorbed. The absorption is dependent on the blood composition, so that the absorption is sensitive to blood flow variations. The optical properties of the dermis are generally the same for all human races. The dermis contains a dense network of blood vessels, about 10% of an adult's total vessel network. These vessels contract according to the blood flow in the body. They consequently change the structure of the dermis, which influences the reflectance of the skin layers. Consequently, the heart rate can be determined from skin reflectance variations, which is the principle underlying the method presented herein.

In the illustrated embodiment of the method, an initialization phase is completed first, in order to determine the appropriate settings for the digital camera 2 (step 17). To this end, the data processing device 3 causes at least one of the frame rate, exposure time, pixel clock (determines the rate at which pixel values are acquired) and gain of the camera channel of the digital camera 2 to be varied whilst a sequence of digital images is captured. The (spatial) average brightness of at least part of each image of the sequence is determined, and the magnitude of the periodic fluctuations in the average brightness is determined for each new value of the settings. Those settings for which the magnitude within at least a range of the spectrum, in particular a low-frequency range, is smallest are selected for subsequent use in the method. Instead of determining the spatial average brightness of at least a part of the image, an individual pixel's brightness fluctuations can be determined. The effect of choosing the settings of the digital camera 2 is that periodic background lighting fluctuations are absent to the largest extent possible from the sequence of images to which the remainder of the method is applied.

In a next step 18, a sequence 19 of images is obtained from the digital camera 2. The sequence 19 of images represents a scene captured at successive points in time, which may be at regular or irregular intervals.

In a next step 20, the images 19 are processed in order to remove non-periodic background signals. To this end, a correction signal corresponding to a time-varying average brightness of part or all of the images 19 is formed. In the illustrated embodiment, the pixel data of the images 19 is then decorrelated from the correction signal. Algorithms for cancelling non-linear cross-correlations are known per se. Further image processing may take place at this stage 20, e.g. to compensate for camera motion.

In two next steps 21,22, an image segmentation algorithm is performed on at least one image of the sequence 19 of digital images. In particular, an algorithm for detecting an image segment 23 representing a body part, generally the face, is carried out in these steps 21,22. A suitable algorithm is described in Viola, P. and Jones, M. J., "Robust real-time object detection", *Proc. of IEEE Workshop on statistical and computational theories of vision,* 13 Jul. 2001. Other suitable algorithms based on recognizing segments with certain shapes and/or colors (skin colors) are known and can be used instead of or in addition to this algorithm. One or more, for example all, distinct segments 23 determined to correspond to a body part of the desired type are tracked (step 24) through the sequence 19 of images. That is to say that the segment 23 is placed, i.e. its location determined, by comparing the images in the sequence 19 to quantify the movement of the body parts within the images 19. A suitable tracking algorithm is known, for example, from De Haan et al., "True-motion estimation with 3-D recursive search block matching", *IEEE Transactions on circuits and systems for video technology*, 3 (5), October 1993, pp. 368-379.

Subsequently, for each selected and tracked segment 23 a measurement zone 26 within the image segment 23 is selected (step 25). This step 25 involves a spatial analysis of the pixel data of a plurality of image parts—each image part being one or more image points in size—to determine a set of contiguous parts determined to have similar characteristics. This step 25 is carried out automatically by the data processing device 3. A suitable algorithm is an algorithm for detecting regions with minimal gradient variations. Those image parts belonging to the region are selected to form the measurement zone 26. In the illustrated embodiment, the position of the measurement zone 26 is determined by analysis of a key image in the sequence 19 of images. Its position relative to the segment 23 corresponding to a body part is determined, and it is thus tracked with the image segment 23 through the sequence 19 of images. Thus, it is determined which pixel of each of the images corresponds to a particular image point of the measurement zone 26 for all image points making up the measurement zone.

Next (step 27), a signal 28 representative of the time-varying average brightness of the pixels corresponding to the image points of the measurement zone 26 is generated. For each image of the sequence 19, the average brightness of the pixels determined to be comprised in the measurement zone 26 is formed. Since each image of the sequence 19 represents a point in time, a time-varying (discrete-time) signal is thus obtained. In an alternative embodiment, certain image points are discarded, so that a sum of pixel values at fewer than all image points in the measurement zone 26 is taken. Moreover, the brightness may be a weighted sum of the color components or only the value of one color component. Green has been found to have the strongest signal.

The signal 28 is then centered on its mean value (step 29) to yield a further signal 30 representative of the time-varying average brightness of pixels corresponding to the image points of the measurement zone 26, the better to observe variations in it. In a variant, this step 29 also comprises the decorrelation with the correction signal that is alternatively comprised in the step 20. In a different variant, this step 29 comprises a filtering operation, e.g. a filtering operation corresponding to differentiation of the signal. Other alternatives for extracting variations of the order of 1% of the first signal's dynamic range are possible.

Finally (step 31) basic signal processing techniques are used to extract information representative of the heart rate or respiration rate from the second signal 30.

Figure 2:
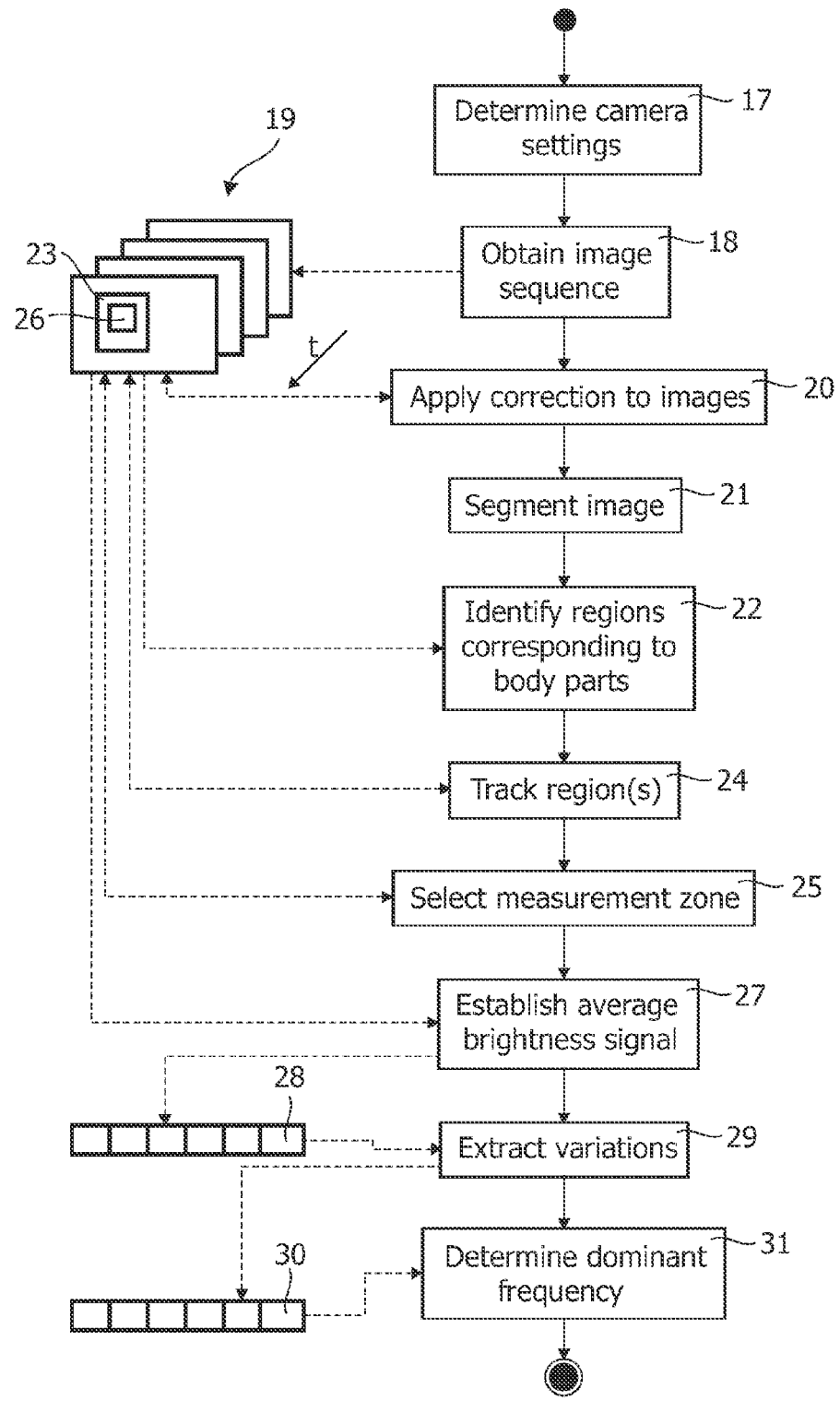
FIG. 2 is a flow chart illustrating a method for determining the heart rate or respiration rate of the living being.

A first application of at least part of the method of FIG. 2 in the system of FIG. 1 involves detecting the presence of a living being, in particular a human being. To this end, an output representative of whether the presence of at least one peak in the spectrum corresponding to a frequency of the periodic physiological phenomenon is detected is used to control one or more of the peripheral devices to perform a function conditional on detecting a presence of at least one human being. In this case, the spectrum, or peaks of the spectrum, in at least a limited range is compared with a pre-determined reference range corresponding to typical human heart rates or respiration rates. If a human being is present, then, for example, the television set 8 and the ambient system can continue to function. If not, they can be switched off or switched to a standby function. Thus, this application is an application in an energy-saving device. A similar application is to intelligent lighting systems for homes and offices. The detection of living beings by means of automated image analysis is less sensitive to false alarms, e.g. due to pets.

A similar application is to control a conditional access system, e.g. one including the biometric scanning device 13. In an embodiment, this can be a fingerprint scanner. Using the detection of living beings, it is ensured that e.g. wax casts of a person's finger cannot be used to fool the conditional access system. A conditional access system using only the camera 2 (e.g. to scan a person's iris or face) can also benefit from the additional use of the method of FIG. 2 to determine that a living person is actually in front of the camera lens.

Alternatively or additionally, the method of FIG. 2 is used to provide biofeedback to a user. More particularly, at least the ambient system is caused to adapt its output in dependence on the frequency determined in the last step 31 of the method. For example, the color or intensity of light emitted by the lighting units 10,11,12 can be changed in dependence on the heart rate. To this end, the method of FIG. 2 is carried out in real-time on a sequence comprising the last N digital images obtained by the data processing device 3. N depends on the image capture rate, and is chosen in dependence on the image capture rate to cover a sequence spanning a time interval long enough to cover at least two heartbeats of an average human being, e.g. at least four seconds long. In a variant, multiple measurement zones 26 are selected, and multiple average signals 30 are established, so that the data processing device 3 is able to determine the current heart rate and/or respiration rate of multiple individuals. Thus, the feedback provided using the ambient system can be made dependent on the heart rate of multiple users.

Figure 3:
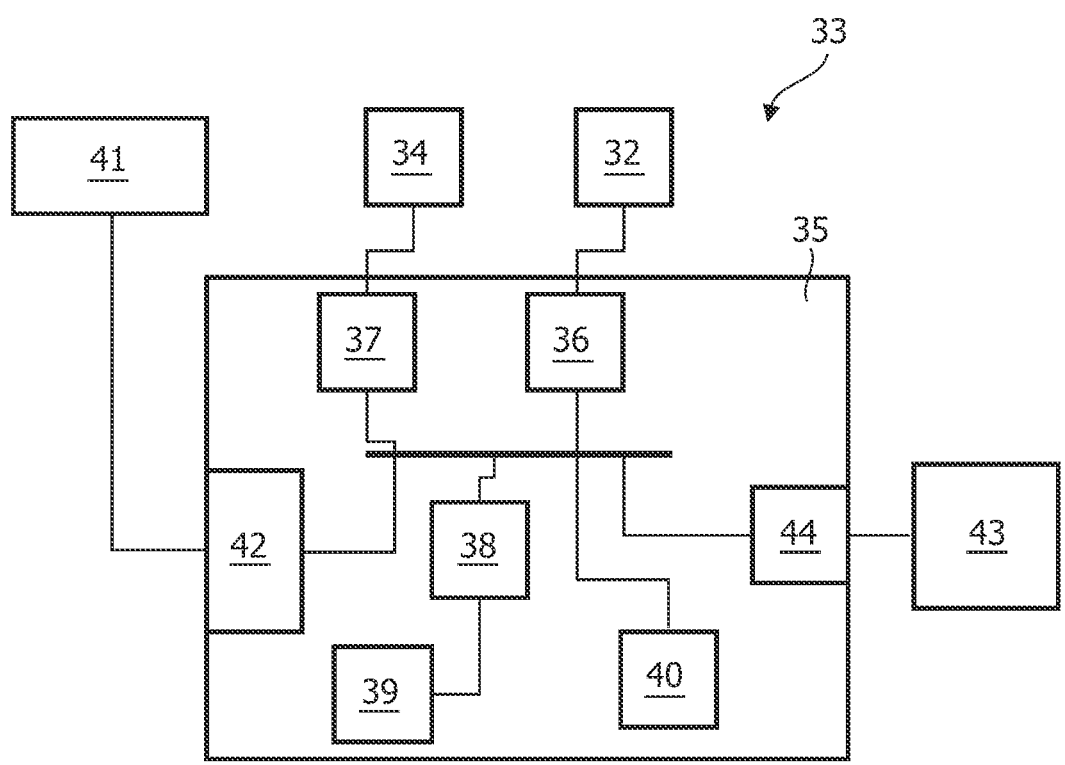
FIG. 3 is a schematic diagram of an imaging system that is gated by a signal obtained by processing a running sequence of images.

An alternative application of at least a part of the method of FIG. 2 involves the use of a system 33 as illustrated schematically in FIG. 3. In this application, the average signal 28 or the signal 30 representative of the time-varying average brightness but centered on the mean value thereof is used as a gating signal for an imaging system. The imaging system can be an MRI (Magnetic Resonance Imaging) or CT (Computer Tomography) scanner system, for example. Such an imaging system captures multiple two-dimensional cross-sectional views of a patient. In order to correct for motion of the patient or the patient's organs, the image capturing process is gated using a signal representative of the periodic physiological phenomenon that causes the periodic movement. In the illustrated system 33, which executes at least the first nine steps 17,18,20-22,24,25,27,29 of the method of FIG. 2, the signal 30 that corresponds to the variations in the average brightness of the automatically selected measurement zone is used to gate an image capturing device 32 and a pulse transmitter 34, which are controlled by a data processing device 35 by means of signals provided through appropriate interfaces 36,37. The data processing device 35 comprises a data processing unit 38, main memory 39 and data storage unit 40. It receives the digital image data recording ambient light reflected off the patient from a digital camera 41 through a further interface 42. Images formed by processing of the data from the image capturing device 32 are displayed on a monitor 43, using an appropriate graphics controller 44. With the method of FIG. 2 (excluding the last step 31), the gating signal for the medical imaging method is obtained in an unobtrusive way. First, the experience for the patient is less stressful, because there are no sensors attached to the patient. Second, wires or sensors cannot affect the operation of the transmitter 34 or image capturing device 32. The process by which the gating signal is acquired is completely automated, so that the attention of the medical personnel is not taken up with selection of the measurement zone 26, and the monitor 43 is used only for the actual medical imaging method. The use of a measurement zone 26 and the averaging over it (step 31) ensures that the gating signal is relatively free from noise. It thus requires little or no filtering.

It should be noted that the above-mentioned embodiments illustrate, rather than limit, the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The mere fact that certain measures are recited in mutually different dependent claims does not indicate that a combination of these measures cannot be used to advantage.

As mentioned, the method outlined herein can be carried out on a single color component of the pixel data or on a weighted sum of two or more of the color components (Red, Green and Blue or Cyan, Magenta, Yellow and Key, for example).

The medical imaging method described with reference to FIG. 3 can also involve the execution of the last step 31 of the method shown in FIG. 2, in which case it is used to control the frequency of a gating signal provided by a signal generator.

The invention claimed is:

1. Method of processing images of at least one living being including:
   obtaining a sequence (19) of digital images taken at consecutive points in time;
   automatically selecting at least one measurement zone (26) comprising a plurality of image points, wherein
   the step (25) of selecting at least one measurement zone (26) includes analyzing information based on pixel data of a plurality of image parts in at least one of the images (19), each image part including at least one image point, and selecting each measurement zone (26) from contiguous image parts determined to have similar characteristics; and
   for each measurement zone (26), obtaining a signal (28,30) representative of at least variations in a time-varying average value of a combination of pixel values at at least a number of the image points for use in determining at least one of a presence and a frequency value of at least one peak in a spectrum of the signal (28,30) corresponding to a frequency of a periodic physiological phenomenon.

2. Method according to claim 1,
   including using a tracking algorithm to place at least one of the measurement zone (26) and an image segment (23) including the measurement zone (26) in each of a plurality of the images in the sequence (19).

3. Method according to claim 1,
   wherein the sequence (19) of digital images is caused to be captured by a camera (2;41) upon completion of an initialization phase (17), the initialization phase (17) including:
   measuring periodic intensity fluctuations in at least parts of images acquired by the camera (2;41) whilst camera settings are varied, and
   selecting values of the camera settings at which measured periodic intensity fluctuations in at least a range of frequencies are determined to be minimal.

4. Method according to claim 1, including:
   determining a correction signal corresponding to a time-varying value of a combination of pixel values at least a number of image points in an image part other than the measurement zone (26), and
   decorrelating at least one of the pixel data of the images in at least the measurement zone (26) and the time-varying average value of the combination of pixel values at at least a number of the image points M the measurement zone (26) from the correction signal.

5. Method according to claim 1,
   wherein the frequency value of at least one peak in the spectrum corresponding to the frequency of the periodic physiological phenomenon is determined and a system (9-12) for providing perceptible output is caused to adapt its output in dependence on the frequency signal.

6. Method according to claim 1, including providing a gating signal based on the signal (28,30) corresponding to at least the variation in the time-varying average value of a combination of pixel values at at least a number of the image points to an imaging system (32,34,35).

7. Method according to claim 1, including:
   selecting a plurality of measurement zones (26);
   for each measurement zone (26), obtaining a signal representative of at least variations in a time-varying average value of a combination of pixel values at at least a number of the image points and determining the frequency value of at least one peak in a spectrum of the signal corresponding to a frequency of a periodic physiological phenomenon; and
   detecting how many living beings are represented in the sequence of images by comparing the frequency values.

8. Method according to claim 1,
   including performing image segmentation on at least one of the sequence (19) of digital images to select pixel data for the analysts included in the selection step (25).

9. Method according to claim 8,
   wherein the image segmentation is performed using an algorithm for recognizing image parts corresponding to at least one type of body part of a living being.

10. Method according to claim 1,
    wherein an output representative of whether the presence of at least one peak in the spectrum corresponding to a frequency of the periodic physiological phenomenon is detected is used to control a device (8,9,13) arranged to perform a function conditional on detecting a presence of at least one living being of at least one kind.

11. Method according to claim 10,
    wherein the output is provided to a conditional access system (3,13) for use in an authentication operation.

12. System for processing images of at least one living being, including:
    a data processing device (3;35) having a processor (5) configured to obtain a sequence (19) of digital images taken at consecutive points, the data processing device configured to:
    automatically select at least one measurement zone (26) comprising a plurality of image points, wherein the image data processing system (3;35) is configured to select the at least one measurement zone (26) by analyzing information based on pixel data of a plurality of image parts in at least one of the images (19), each image part including at least one image point, and to select each measurement zone (26) from contiguous image parts determined to have similar characteristics; and
    for each measurement zone (26), to obtain a signal (28, 30) representative of at least variations in a time-varying value of a combination of pixel values at at least a number of the image points for use in determining at least one of a presence and a frequency value of at least one peak, in a spectrum of the signal (28,30) corresponding to a frequency of a periodic physiological phenomenon.

13. System according to claim 12,
the processor (5) using a tracking algorithm to place at least one of the measurement zone (26) and an image segment (23) including the measurement zone (26) in each of a plurality of the images in the sequence (19).

14. System according to claim 12,
wherein the sequence (19) of digital images is caused to be captured by a camera (2;41) upon completion of an initialization phase (17), the initialization phase (17) including:
measuring periodic intensity fluctuations in at least parts of images acquired by the camera (2;41) whilst camera settings are varied, and
selecting values of the camera settings at which measured periodic intensity fluctuations in at least a range of frequencies are determined to be minimal.

15. System according to claim 12, including the processor (5):
determining a correction signal corresponding to a time-varying value of a combination of pixel values at at least a number of image points in an image part other than the measurement zone (26), and
decorrelating at least one of the pixel data of the images in at least the measurement zone (26) and the time-varying average value of the combination of pixel values at at least a number of the image points in the measurement zone (26) from the correction signal.

16. System according to claim 12,
wherein the frequency value of at least one peak in the spectrum corresponding to the frequency of the periodic physiological phenomenon is determined and a system (9-12) for providing perceptible output is caused to adapt its output in dependence on the frequency signal.

17. System according to claim 12, including providing a gating signal based on the signal (28,30) corresponding to at least the variation in the time-varying average value of a combination of pixel values at at least a number of the image points to an imaging system (32,34,35).

18. System according to claim 12, including the processor (5):
selecting a plurality of measurement zones (26);
for each measurement zone (26), obtaining a signal representative of at least variations in a time-varying average value of a combination of pixel values at at least a number of the image points and determining the frequency value of at least one peak in a spectrum of the signal corresponding to a frequency of a periodic physiological phenomenon; and
detecting how many living beings are represented in the sequence of images by comparing the frequency values.

19. System according to claim 12,
the processor (5) performing image segmentation on at least one of the sequence (19) of digital images to select pixel data for the analysis included in the selection step (25).

20. System according to claim 19,
wherein the image segmentation is performed using an algorithm for recognizing image parts corresponding to at least one type of body part of a living being.

21. System according to claim 12,
wherein an output representative of whether the presence of at least one peak in the spectrum corresponding to a frequency of the periodic physiological phenomenon is detected is used to control a device (8,9,13) arranged to perform a function conditional on detecting a presence of at least one living being of at least one kind.

22. System according to claim 21,
wherein the output is provided to a conditional access system (3,13) for use in an authentication operation.

23. Method of processing images of at least one living being, including:
obtaining a sequence (19) of digital images taken at consecutive points in time;
selecting at least one measurement zone (26) comprising a plurality of image points, wherein
the step (25) of selecting at least one measurement zone (26) includes analyzing information based on pixel data of a plurality of image parts in at least one of the images (19), each image part including at least one image point, and selecting each measurement zone (26) from contiguous image parts determined to have similar characteristics; and
for each measurement zone (26), obtaining a signal (28, 30) representative of at least variations in a time-varying average value of a combination of pixel values at at least a number of the image points for use in determining at least one of a presence and a frequency value of at least one peak in a spectrum of the signal (28,30) corresponding to a frequency of a periodic physiological phenomenon;
determining a correction signal corresponding to a time-varying value of a combination of pixel values at at least a number of image points in an image part other than the measurement zone (26), and
decorrelating at least one of the pixel data of the images in at least the measurement zone (26) and the time-varying average value of the combination of pixel values at at least a number a the image points in the measurement zone (26) from the correction signal.

24. Method of processing images of at least one living being, including:
obtaining a sequence (19) of digital images taken at consecutive points in time;
selecting at least one measurement zone (26) comprising a plurality of image points, wherein
the step (25) of selecting at least one measurement zone (26) includes analyzing information based on pixel data of a plurality of image parts in at least one of the images (19), each image part including at least one image point, and selecting each measurement zone (26) from contiguous image parts determined to have similar characteristics; and
for each measurement zone (26), obtaining a signal (28, 30) representative of at least variations in a time-varying average value of a combination of pixel values at at least a number of the image points for use in determining at least one of a presence and a frequency value of at least one peak in a spectrum of the signal (28,30) corresponding; to a frequency of a periodic physiological phenomenon,
wherein the frequency value of at least one peak in the spectrum corresponding to the frequency of the periodic physiological phenomenon is determined and a system (9-12) for providing perceptible output is caused to adapt its output in dependence on the frequency signal.

25. Method of processing images of a least one living being, including:
obtaining a sequence (19) of digital images taken at consecutive points time;

selecting at least one measurement one (26) comprising a plurality of image points, wherein the step of (25) of select at as one measurement one (26) includes analyzing information based on pixel data of a plurality of image parts in at least one of the images (19), each image part including at least one image point, and selecting each measurement zone (26) from contiguous image parts determined to have similar characteristics; and for each measurement zone (26), obtaining a signal (28, 30) representative of at least variations in a time-varying average value of a combination of pixel values at at least a number of the image points for use in determining at least one of a presence and a frequency value of at least one peak in a spectrum of the signal (28,30) corresponding to a frequency of a periodic physiological phenomenon, providing a gating, signal based on the signal (28,30) corresponding to at least the variation in the time-varying average value of a combination of pixel values at at least a number or the image points to an imaging system (32,34,35).

26. Method of processing images of at least one living being, including:

obtaining a sequence (19) of digital images taken at consecutive points in time;

selecting at least one measurement zone (26) comprising a plurality of image points, wherein the step (25) of selecting at least one measurement zone (26) includes analyzing information based on pixel data of a plurality of image parts in at least one of the images (19), each image part including at least one image point, and selecting each measurement zone (26) from contiguous image parts determined to have similar characteristics; and for each measurement zone (26), obtaining a signal (28, 30) representative of at least variations in a time-varying average value of a combination of pixel values at at least a number of the image points for use in determining at least one of a presence and a frequency value of at least one peak in a spectrum of the signal (28,30) corresponding to a frequency of a periodic physiological phenomenon, selecting a plurality of measurement zones (26);

for each measurement zone (26), obtaining a signal representative of at least variations m a time-varying average value of a combination of pixel values at at least a number of the image points and determining the frequency value of at least one peak in a spectrum of the signal corresponding to a frequency of a periodic physiological phenomenon; and detecting how many living beings are represented in the sequence of images by comparing the frequency values.

27. Method of processing images of at least one living being, including:

obtaining a sequence (19) of digital images taken at consecutive points in time selecting at least one measurement zone (26) comprising a plurality of image points, wherein the step (25) of selecting at least one measurement zone (26) includes analyzing information based on pixel data of a plurality of image parts in at least one of the images (19), each image part including at least one image point, and selecting each measurement zone (26) form contiguous image pans determined to have similar characteristics; and for each measurement zone (26), obtaining a signal (28, 30) representative of at least variations in a time-varying average value of as combination of pixel values at at least a number of the image points for use in determining at least one of a presence and a frequency value of at least one peak in a spectrum of the signal (28,30) corresponding to a frequency of a periodic physiological phenomenon, wherein an output representative of whether the presence of at least one peak in the spectrum corresponding to a frequency of the periodic physiological phenomenon is detected is used to control a device (8,9,13) arranged to perform a function conditional on detecting a presence of at least one living being of at least one kind.

28. Method according to claim 27, wherein the output is provided to a conditional access system (3,13) for use in at authentication operation.

* * * * *